United States Patent
Tiernan et al.

(10) Patent No.: US 9,678,175 B2
(45) Date of Patent: Jun. 13, 2017

(54) EDDY CURRENT DETECTION

(75) Inventors: Timothy C. Tiernan, Newton, MA (US); Mark Steinback, Newton, MA (US); Noa M. Rensing, Newton, MA (US); Evan Weststrate, Norwood, MA (US)

(73) Assignee: Radiation Monitoring Devices, Inc., Watertown, MA (US)

( * ) Notice: Subject to any disclaimer, the term of this patent is extended or adjusted under 35 U.S.C. 154(b) by 539 days.

(21) Appl. No.: 13/166,729

(22) Filed: Jun. 22, 2011

(65) Prior Publication Data

US 2012/0019236 A1  Jan. 26, 2012

Related U.S. Application Data

(60) Provisional application No. 61/367,648, filed on Jul. 26, 2010.

(51) Int. Cl.
| | |
|---|---|
| *G01N 27/72* | (2006.01) |
| *G01R 33/09* | (2006.01) |
| *G01N 27/90* | (2006.01) |
| *G01B 1/00* | (2006.01) |
| *G01N 1/00* | (2006.01) |

(52) U.S. Cl.
CPC .......... *G01R 33/09* (2013.01); *G01N 27/9033* (2013.01); *G01R 33/096* (2013.01); *G01B 1/00* (2013.01); *G01B 2210/00* (2013.01); *G01N 1/00* (2013.01)

(58) Field of Classification Search
CPC ........ G01N 1/00; G01N 2201/00; G01R 1/00; G01B 1/00; G01B 2210/00

USPC ....... 324/221, 228, 232, 235, 262, 263, 529, 324/754.17, 754.21, 754.29, 555, 718,
(Continued)

(56) References Cited

U.S. PATENT DOCUMENTS

| | | | |
|---|---|---|---|
| 3,192,474 A | * | 6/1965 | Cherry ..................... G01N 3/00 219/109 |
| 4,016,487 A | | 4/1977 | Neumaier |

(Continued)

FOREIGN PATENT DOCUMENTS

| | | |
|---|---|---|
| GB | 1512201 | 5/1978 |
| JP | 09-507294 A | 7/1997 |

(Continued)

OTHER PUBLICATIONS

International Search Report and Written Opinion for International Application No. PCT/US2011/044812, mailed Nov. 18, 2011.

(Continued)

*Primary Examiner* — Jermele M Hollington
*Assistant Examiner* — Temilade Rhodes-Vivour
(74) *Attorney, Agent, or Firm* — Wolf, Greenfield & Sacks, P.C.

(57) ABSTRACT

Eddy current detection probes and related methods are disclosed. In some embodiments, the eddy current detection probes are hybrid probes, including a solid state sensor and a detection loop. In some embodiments, the eddy current detection probes include a drive coil and a detection loop, with the detection loop having a sensitive axis that is not parallel to principal axis of the drive coil. In some such embodiments, the sensitive axis of the detection loop is perpendicular to the principal axis of the drive coil.

9 Claims, 13 Drawing Sheets

(58) Field of Classification Search
USPC ..... 324/222, 234, 236–243, 251–252, 207.2, 324/207.21
See application file for complete search history.

(56) References Cited

U.S. PATENT DOCUMENTS

| | | | | |
|---|---|---|---|---|
| 4,998,065 | A * | 3/1991 | Koizumi | G01B 1/00 324/309 |
| 5,262,722 | A | 11/1993 | Hedengren et al. | |
| 6,040,695 | A | 3/2000 | Raulerson et al. | |
| 6,232,774 | B1 * | 5/2001 | Kimura | G01N 27/82 324/232 |
| 6,344,741 | B1 | 2/2002 | Giguere et al. | |
| 6,377,040 | B1 | 4/2002 | Hell | |
| 6,791,319 | B2 | 9/2004 | Hiroshima | |
| 2002/0163333 | A1 * | 11/2002 | Schlicker | G01N 27/902 324/242 |
| 2003/0071615 | A1 | 4/2003 | Schlicker et al. | |
| 2004/0075429 | A1 | 4/2004 | Hiroshima | |
| 2004/0152310 | A1 | 8/2004 | Swedek et al. | |
| 2004/0189293 | A1 * | 9/2004 | Czipott | G01V 3/15 324/244 |
| 2005/0007108 | A1 * | 1/2005 | Dogaru | 324/235 |
| 2005/0264284 | A1 * | 12/2005 | Wang | G01N 27/904 324/240 |
| 2007/0053554 | A1 * | 3/2007 | Fayad | A61B 5/055 382/128 |
| 2007/0096727 | A1 | 5/2007 | Rempt et al. | |
| 2007/0188168 | A1 * | 8/2007 | Stanley | B60R 21/0136 324/228 |
| 2007/0222433 | A1 * | 9/2007 | Tiernan et al. | 324/207.21 |
| 2008/0258722 | A1 | 10/2008 | Zon et al. | |
| 2009/0167298 | A1 * | 7/2009 | Kreutzbruck | G01N 27/9033 324/235 |
| 2009/0192755 | A1 | 7/2009 | Sheiretov et al. | |
| 2009/0206831 | A1 * | 8/2009 | Fermon | G01N 27/9046 324/240 |
| 2012/0007595 | A1 * | 1/2012 | Lepage | G01N 27/9006 324/239 |
| 2012/0206132 | A1 * | 8/2012 | Lepage | G01N 27/9033 324/239 |

FOREIGN PATENT DOCUMENTS

| | | |
|---|---|---|
| JP | 2001-324479 A | 11/2001 |
| JP | 2006-322860 A | 11/2006 |
| JP | 2009-210399 A | 9/2009 |
| JP | 4464758 | 5/2010 |
| JP | 4575029 | 11/2010 |

OTHER PUBLICATIONS

Japanese Office Action dated Nov. 4, 2014 in connection with Application No. 2013-521834.

* cited by examiner

EDDY CURRENT DETECTION

RELATED APPLICATIONS

The present application claims the benefit under 35 U.S.C. 119(e) to U.S. Provisional Patent Application Ser. No. 61/367,648, filed on Jul. 26, 2010 and entitled "Eddy Current Detection", which is incorporated herein by reference in its entirety.

BACKGROUND

Field

The present application discloses various aspects relating to eddy current detection technology.

Related Art

In general, materials may have defects (or flaws) in them, such as cracks, inclusions and corrosion. The defects may form for various reasons, including as a result of manufacturing and/or stresses experienced by the material over its lifetime.

One manner for detecting such defects in a conductive material (such as a metal or metal alloy) is to generate eddy currents within the material and detect the resulting magnetic fields. Eddy currents are generated in a conductive material in response to a suitable time varying magnetic field being applied to the conductive material. The time varying magnetic field gives rise to a force on the electrons in the conductive material, thus creating current, referred to as "eddy current." The eddy currents themselves give rise to magnetic fields, referred to as induced magnetic fields, which oppose the incident magnetic field. The distributions of the eddy currents will be altered by cracks (or other defects) in the material, thus creating perturbations in the induced magnetic fields. The changes in the induced magnetic fields, which are detected with an eddy current probe, give an indication of the presence of the cracks (or other defects) and their characteristics (e.g., location, size, shape, etc.). Generally, the magnetic field due to the coil as well as the magnetic fields arising from the eddy currents induced in a uniform material have a well characterized spatial distribution which is exactly axial at the center of the current loop and has field lines that surround the current distribution. The magnetic fields has both radial and axial components, and near the center the in plane component is very small. For a circular coil and a uniform material, the tangential component of both direct and induced magnetic fields is zero. In contrast, if there are cracks or other irregularities in the material which disrupt the eddy currents and perturb the magnetic field, the induced magnetic field may be modified and may have substantial in-plane components and possibly substantial tangential components. These in-plane components may be easier to detect than changes in the substantial axial magnetic field.

This effect may be especially pronounced if the position of the crack or flaw relative to the coil is such that the maximum eddy current density would pass through that point in the absence of the flaw, and if the characteristic depth of the eddy current distribution is comparable to or smaller than the extent of the crack or flaw in the depth direction.

Conventional coil-based eddy current probes generally take one of two forms. A first type of conventional coil-based eddy current probe uses a single coil (i.e., a combined drive/detection coil) to both carry the current that generates (or drives) the incident magnetic field applied to the conductive material under test and detect the magnetic field due to the eddy currents in the material under test. Monitoring this field allows the instrument to detect changes caused by cracks or other flaws. A second type of conventional coil-based eddy current probe uses two distinct co-axial coils— one which carries the current that generates (or drives) the incident magnetic field applied to the conductive material under test and a second which detects the total magnetic field and can be monitored to detect changes due to cracks (or other defects) in the material under test.

FIG. 1 illustrates a conventional coil-based eddy current probe of the first type. The probe 100 includes a single coil 102 through which an alternating current (AC) current is applied to generate a magnetic field incident upon a conductive material under test 104 when the probe is placed in proximity to the material under test. The incident magnetic field gives rise to eddy currents in the material under test 104 as shown which generate a magnetic flux which passes through the coil 102. A crack (or other type of defect) 106 in the material under test 104 disturbs the eddy currents 108 and therefore the magnetic flux. The disturbance in the magnetic flux thus indicates the presence of the crack (or other type of defect).

FIG. 2 illustrates a conventional coil-based eddy current probe of the second type. As shown, the probe 200 includes two distinct but co-axial coils, a drive coil 202 to generate the eddy currents in the material under test by applying an incident magnetic field and a detection coil 204 (of one or more turns) to detect the magnetic flux resulting from the eddy current. Because the coils 202 and 204 are co-axial, the sensitive axis of the detection coil is parallel to the principal axis of the drive coil (i.e., the primary direction of the magnetic field generated by the drive coil).

It should be appreciated from FIGS. 1 and 2 that both of these types of conventional coil-based eddy current probes use a detection coil that is sensitive to the magnetic field components oriented in the same direction as the magnetic fields created by the drive coil. These fields are generally oriented in the direction normal to the surface of the material under test.

In the case of a two coil eddy current sensor, however, the detection coil may alternately be arranged with its axis at an angle to the drive coil axis, so as to be more sensitive to in plane components of the magnetic field or specifically to the tangential direction or to in-plane components (either tangential or radial) at the center of the coil, or to reduce its sensitivity to the out-of-plane component of the magnetic field.

Some conventional eddy current probes do not use a detection coil, and instead use a solid-state magnetic field detecting element. These include magneto-resistive sensors (such as anisotropic (AMR) or giant magnetoresistive sensors), Hall Effect sensors, and superconducting quantum interference devices (SQUIDS). In the case of magnetoresistive sensors, the resistance of the sensor varies depending on the magnetic field applied to the sensor. Thus, when an AMR sensor is placed in the presence of an eddy current, the magnetic fields generated by the eddy current may alter the resistance value of the AMR sensor. The alteration in the resistance value is used to detect the presence and strength of the eddy currents and thus of any defects in the material under test.

SUMMARY

Eddy current detection probes and related methods are disclosed.

In one aspect, an eddy current detection probe is provided. The probe includes a solid state sensor configured to sense changes in a magnetic field created by perturbations in an eddy current. The probe further includes a conductive detection loop configured to receive the magnetic field and generate a voltage in response to variation in the magnetic field.

In one aspect, an eddy current detection probe is provided. The probe includes a substrate having a substantially planar surface and a drive coil disposed on the substantially planar surface. The probe further includes an anisotropic magnetoresistive (AMR) sensor disposed on the substantially planar surface of the substrate and positioned within a perimeter of the drive coil. The probe further includes a detection loop comprising a first electrical lead and a second electrical lead. The first electrical lead is connected to a first end of the AMR sensor and the second electrical lead is connected to a second end of the AMR sensor. The first electrical lead and the second electrical lead are positioned at least partially around the substrate to form the detection loop. The detection loop is substantially perpendicular to the drive coil.

In one aspect, an eddy current probe is provided. The probe includes a first substrate having a substantially planar surface and a drive coil disposed on the substantially planar surface of the first substrate. The probe includes a second substrate smaller than the first substrate. The second substrate has a substantially planar surface. The probe includes an anisotropic magnetoresistive (AMR) sensor disposed on the substantially planar surface of the second substrate and attached to the first substrate within a perimeter of the drive coil. The probe further includes a detection loop comprising a first electrical lead and a second electrical lead. The first electrical lead is connected to a first end of the AMR sensor and the second electrical lead is connected to a second end of the AMR sensor. The first electrical lead and second electrical lead are positioned at least partially around the first substrate to form the detection loop. The detection loop is substantially perpendicular to the drive coil.

In one aspect, an eddy current detection probe is provided. The probe includes a drive coil and a conductive detection loop oriented substantially perpendicular to the drive coil. The conductive detection loop has a height that is substantially perpendicular to the drive coil and less than 2.5 mm. In some embodiments, the conductive detection loop has a height that is less than 0.5 mm.

In one aspect, a method is provided. The method comprises exciting a drive coil of an eddy current detection probe with an alternating current (AC) signal having a frequency greater than approximately 1 MHz and applying to a material under test an incident magnetic field generated by the drive coil as a result of exciting the drive coil. The method further comprises detecting an induced magnetic field from the material under test using a conductive detection loop oriented substantially perpendicular to the drive coil.

In one aspect, a method of manufacturing an eddy current probe is provided. The method comprises fabricating a conductive drive coil on a first layer of a multi-layered substrate; and fabricating conductive traces on at least two layers of the multi-layered substrate. The method further comprises interconnecting with conductive material the conductive traces on the at least two layers of the multi-layered substrate to form a detection loop substantially perpendicular to the conductive drive coil.

In one aspect, a probe for depth profiling is provided. The probe comprises a drive coil configured to be positioned proximate a surface of an article being tested such that an axis of the drive coil is perpendicular to the surface of the article. The probe further comprises a magnetoresistive sensor constructed and aligned to respond to electrical conductivity and/or magnetic permeability differences between material in a layer at the surface of the article and material in the interior of the article.

Other aspects, embodiments and features of the invention will become apparent from the following detailed description of the invention when considered in conjunction with the accompanying drawings. The accompanying figures are schematic and are not intended to be drawn to scale. In the figures, each identical, or substantially similar component that is illustrated in various figures is represented by a single numeral or notation. For purposes of clarity, not every component is labeled in every figure. Nor is every component of each embodiment of the invention shown where illustration is not necessary to allow those of ordinary skill in the art to understand the invention.

DETAILED DESCRIPTION

Figure 1:
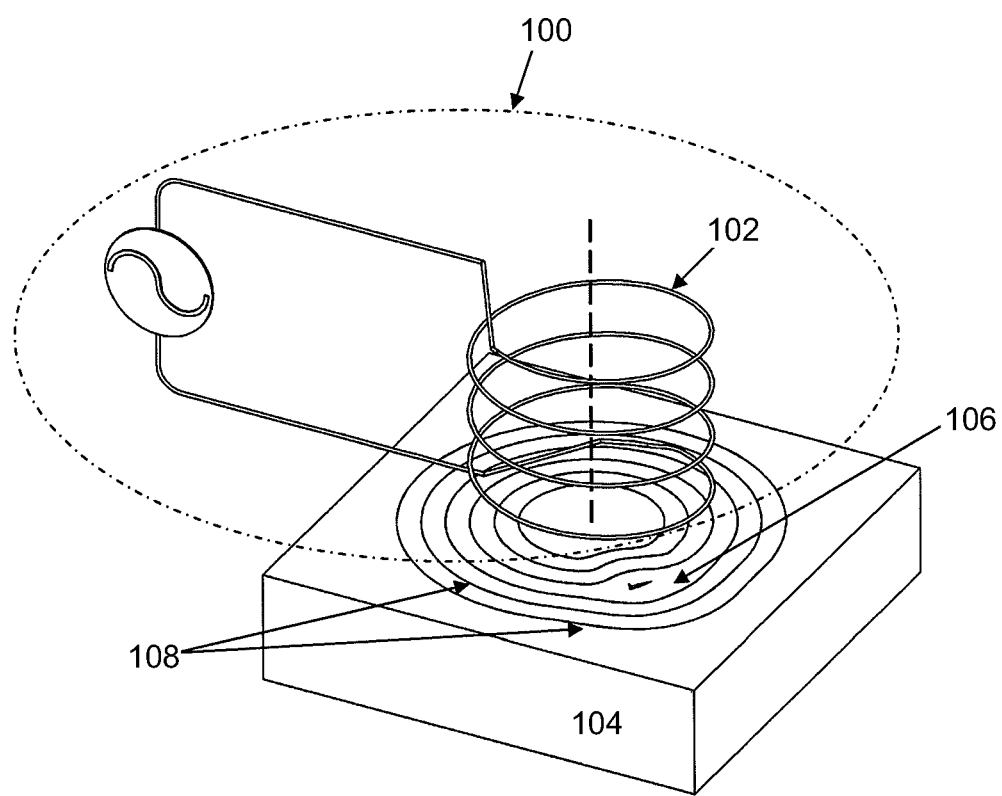
FIG. 1 illustrates a first type of conventional coil-based eddy current probe having a combined drive/detection coil.

The inventors have appreciated that conventional eddy current probes are not without drawbacks in at least some operating scenarios. For example, a problem with conventional coil-based eddy current probes is that, as described above, the orientation of the detection coil is such that the detection coil is sensitive to the magnetic fields directly generated by the drive coil. Because the magnetic fields generated by the drive coil are typically much larger than the magnetic field disturbances associated with cracks (or other defects) in a material under test, conventional coil-based eddy current probes may have difficulty in detecting such cracks (or other defects). Also, in the case of conventional single-coil based eddy current probes (i.e., an eddy current probe using a combination drive/detection coil), the design parameters of the detection circuit cannot be optimized independently of the parameters of the drive circuit.

The use of an AMR sensor may address some problems with respect to conventional coil-based eddy current probes. Namely, the AMR sensor can be oriented to be insensitive to the magnetic field produced by the drive coil. However, the inventors have appreciated the signal from magnetoresistive sensors, including AMR sensors, is frequency independent, while the signal from coil sensors increases linearly with frequency. Thus at higher frequencies (e.g. above 1 MHz) used, for example, for analyzing thin structures or materials with low conductivities, the signal from the coil based sensors may be substantially higher than the signal from an AMR sensor. Conversely, at low frequencies, used for example to examine materials with high conductivities or defects buried more deeply beneath the surface, the AMR sensor signal may be higher than that from a coil based detector.

According to one aspect of the invention, a hybrid eddy current detection probe is provided that includes both a solid state sensor (e.g., an AMR sensor) and a detection loop. The solid state sensor may be configured to be responsive to specific components of a magnetic field produced by eddy currents, which in some situations may result from an incident magnetic field applied by the probe. The detection loop may be responsive to components of magnetic flux associated with the magnetic field produced by the eddy currents. Thus, each of the solid state sensor and the detection loop may provide an output signal (also referred to herein as a "detection signal") indicative of the magnetic field produced by the eddy currents. In some non-limiting embodiments, a combined output signal including a contribution from the solid state sensor and a contribution from the detection loop may be provided by the probe. The sensor may be configured to be especially sensitive to magnetic field components associated with perturbations to the eddy current flow paths associated with cracks or other irregularities in the material, e.g. corrosion damage, inclusions, surface roughness, or other flaws.

In some aspects of the invention, an eddy current detection probe is provided that includes a drive coil and a detection loop having a sensitive axis that is not parallel to the direction of the magnetic field generated by the drive coil. In some non-limiting embodiments, the detection loop may be oriented substantially perpendicular to the drive coil such that the sensitive axis of the detection loop may be substantially perpendicular to the direction of a magnetic field generated by the drive coil and to the induced magnetic field generated in a uniform substrate in the absence of cracks or other irregularities, and would thus only be sensitive to fields disturbances arising from such cracks or irregularities. However, not all embodiments are limited in this respect, as the drive coil and detection loop may have any suitable non-aligned orientation relative to each other. In some embodiments (e.g., when the detection loop is oriented substantially perpendicular to the drive coil), the detection loop has a small height (e.g., less than 2.5 mm, less than 1.0 mm or less than 0.5 mm) which corresponds to the dimension of the loop that is substantially perpendicular to the drive coil. Such a construction enables the probe to have a small size which can enhance performance as described further below.

According to another aspect of the invention, a method of operating an eddy current detection probe is provided. The method comprises exciting a drive coil of the eddy current detection probe with an alternating current (AC) signal having a high frequency (e.g., greater than approximately 1 MHz) and applying to a material under test an incident magnetic field generated by the drive coil as a result of exciting the drive coil. The method further comprises detecting an induced magnetic field from the material under test using a conductive detection loop oriented substantially perpendicular to the drive coil. The use of the high frequency excitation signal may facilitate detection of cracks in low conductivity materials under test and may increase an output signal of the detection loop compared to if lower frequencies of the AC excitation signal were used.

According to another aspect of the present invention, a method of manufacturing an eddy current detection probe comprises manufacturing a drive coil and/or detection loop of the probe on a multi-layered substrate. According to one embodiment, conductive traces on various ones of the multiple layers of the substrate are connected using conductive interconnects to form the drive coil and/or detection loop.

The above-described aspects, as well as additional aspects, are now described in greater detail. These aspects can be used independently, all together, or in any combination of two or more.

Figure 3:
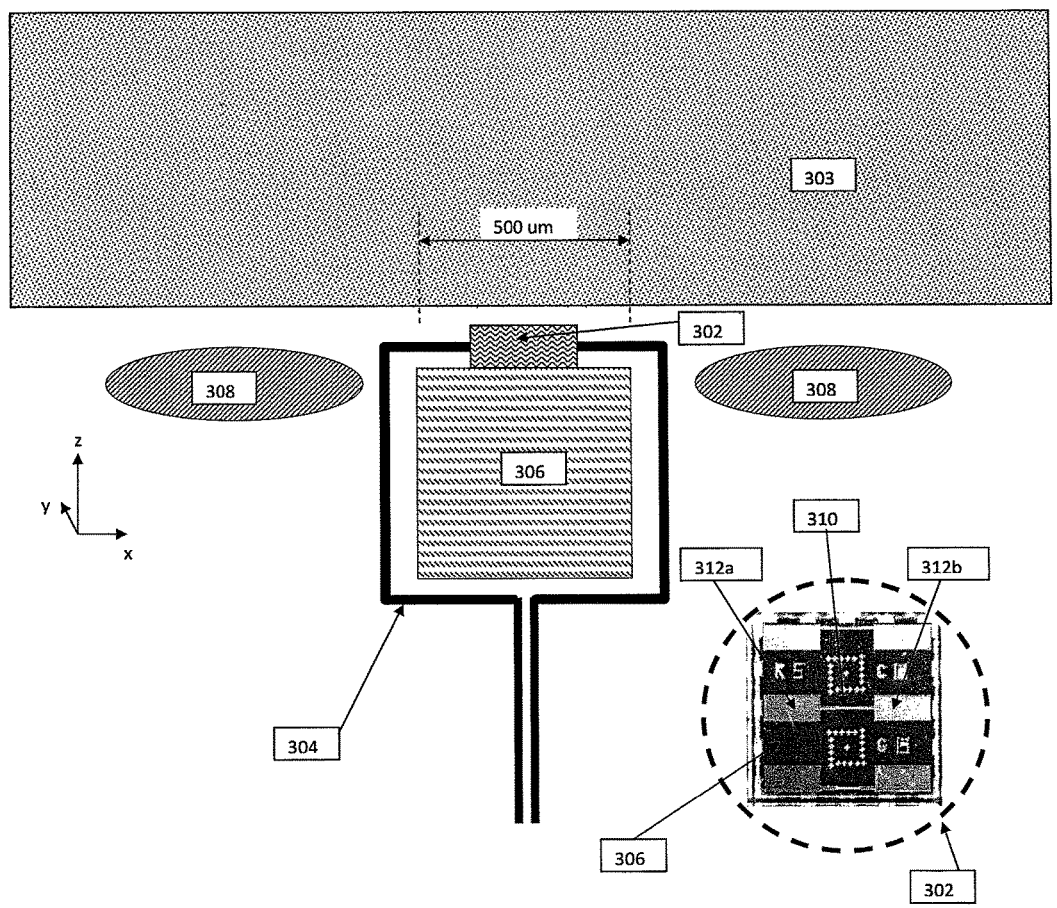
FIG. 3 is a non-limiting example of an eddy current detection probe including a solid state sensor and a conducting loop, according to one non-limiting embodiment.

As mentioned, according to one aspect, an eddy current detection probe comprises both a solid state sensor and a detection loop, and thus may be considered a hybrid eddy current detection probe. FIG. 3 illustrates a side view of a non-limiting example. As shown, the eddy current detection probe 300 includes both a solid state sensor 302 and a detection loop 304. The probe 300 further includes a substrate 306 on which the solid state sensor is disposed, and a drive coil 308.

The solid state sensor 302 may be any suitable solid state sensor for detecting magnetic fields. According to one non-limiting embodiment, the solid state sensor is an AMR sensor. According to one non-limiting embodiment, the solid state sensor 302 is a GMR sensor. Other types of solid state sensors may also be used, as AMR sensors and GMR sensors represent non-limiting examples. Optionally the solid state sensor may be biased so as to influence the direction of sensitivity and/or to linearize its output signal. Biasing may be provided using permanent magnets, conductive "barber-pole stripes" or by any other means known in the art. In some embodiments, the solid state sensor (e.g., AMR sensor) may be configured to be sensitive to magnetic fields along only one axis.

As shown, the solid state sensor 302 may be disposed on a substrate 306. In some embodiments, the substrate 306 may have a substantially planar surface and the solid state sensor 302 may be disposed on the substantially planar surface. It should be understood that other embodiments may include non-planar substrate surfaces. The substrate may be formed of a material that is not magnetically reactive, so as to minimize the impact of the substrate on the probe function. In some embodiments, the substrate 306 may be formed of silicon, though other suitable substrate material may also be used.

The inset of FIG. 3 illustrates a non-limiting example of a top view of a configuration of the solid state sensor 302.

As shown, the solid state sensor may comprise a strip 310 between pads 312a and 312b, and thus may be termed a "strip sensor". The sensor may be disposed on the substrate 306. In one such embodiment, the solid state sensor 302 is an AMR sensor, though not all embodiments are limited to using AMR sensors as the solid state sensor.

The solid state sensor 302 may be configured in any suitable manner for detecting magnetic field components arising from cracks or irregularities in the substrate, i.e., perturbed magnetic fields. For example, the solid state sensor 302 may be arranged to have one or more of its sensitive axes in any suitable relationship with respect to the anticipated direction of the perturbed magnetic fields. As a non-limiting example, the eddy current detection probe 300 may be arranged with the drive coil 308 substantially parallel to the surface of a material under test. In such an arrangement, the magnetic field generated by the drive coil and the magnetic field induced in a uniform material may both be incident substantially perpendicular to the surface of the material under test (i.e., in the z-direction in FIG. 3). Cracks (or other types of defects) in the material under test may be expected to generate induced magnetic fields having components in the x-y plane of FIG. 3, and thus the solid state sensor 302 may be configured to have one or more (if there is more than one) sensitive axis arranged in the x-y plane.

In some embodiments, the solid state sensor 302 may be configured to minimize detection of magnetic fields generated by the drive coil (i.e., incident magnetic fields). In this manner, the ability of the solid state sensor to detect perturbed magnetic fields may be increased. According to one such embodiment, the solid state sensor is dimensioned to have only one sensitive axis, thus allowing for the sensor to more easily be oriented to be insensitive to the magnetic fields generated by the drive coil (as opposed to if the sensor had two or more sensitive axes, which would make it more difficult to arrange the sensor such that each sensitive axis is insensitive to the magnetic fields generated by the drive coil). As an example, the solid state sensor 302 may be an AMR sensor and may be dimensioned to have only one sensitive axis. Such dimensioning may involve making the AMR sensor sufficiently small in two of the three dimensions (e.g., sufficiently narrow in the y-direction of FIG. 3 and sufficiently thin in the z-direction of FIG. 3) to result in only one of the dimensions (e.g., that along the x-axis of FIG. 3) being sensitive to magnetic fields.

However, it should be appreciated that eddy current detection probes of the type illustrated in FIG. 3 are not limited to having a solid state sensor with only one sensitive axis and are not limited to dimensioning the solid state sensor in any particular manner, as the example given above is merely provided for purposes of illustration. Furthermore, at the center of the coil both the incident magnetic field and the magnetic field due to eddy currents induced in a uniform material are exactly perpendicular to the surface, allowing a sensor with more than one in-plane sensitive axis in the plane to be placed there without sensing the incident magnetic field.

The solid state sensor 302 may be configured to minimize its sensitivity to the magnetic fields generated by the drive coil 308 by positioning it suitably relative to the drive coil and by orienting its sensitive axis (or axes) appropriately for its position relative to the drive coil. For example, according to one non-limiting embodiment, the solid state sensor 302 may be substantially centered within the drive coil 308 where the in-plane components of the magnetic field generated by the drive coil are low, and may be centered on the principal axis of the drive coil so that any residual in-plane components of the magnetic field generated by the drive coil average to zero due to symmetry over the volume of the sensor. By arranging the solid state sensor in this manner, the majority or entirety of any output signal ("detection signal") from the solid state sensor may be attributable to perturbed magnetic fields from a non-circular distribution of eddy currents in a material under test and not to the incident magnetic field generated by the drive coil 308. However, not all embodiments are limited to utilizing this particular positioning of the solid state sensor relative to the drive coil. There may be other positions relative to the drive coil where one or more components of the incident field are low and the sensor 302 may be placed there by a suitable choice of orientation of its sensitive direction.

Figure 4:
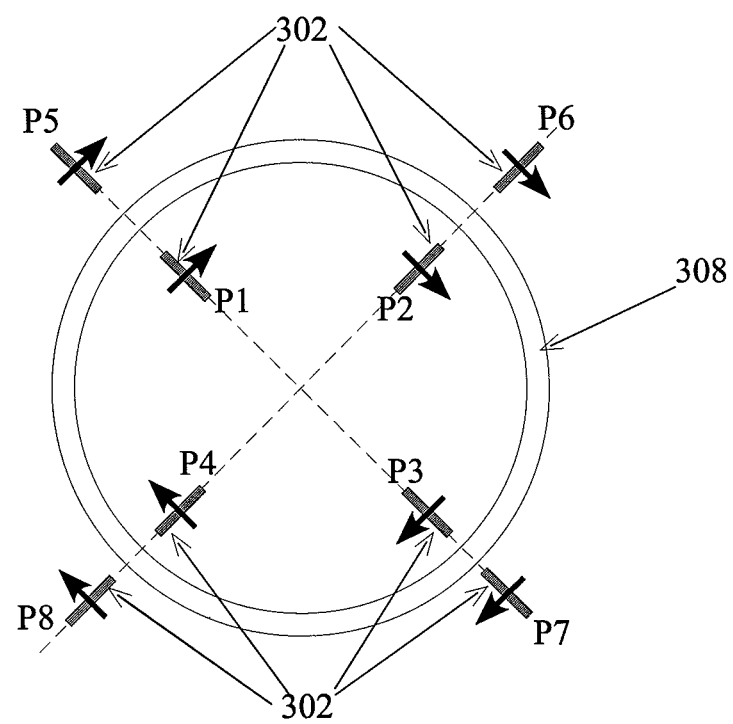
FIG. 4 illustrates an example of four different locations of a solid state sensor relative to a drive coil of an eddy current detection probe according to one non-limiting embodiment.

In one such embodiment, the solid state sensor may be positioned with its sensitive axis tangential to the geometry of the drive coil. For example, in those embodiments in which the solid state sensor is sensitive along only one of its axes, the sensor may be positioned with its insensitive in-plane (i.e., in the plane of the drive coil) direction coincident with a diameter of a circular drive coil and its out-of-plane direction parallel to the principal axis of the drive coil (i.e., in the z-direction in FIG. 3). FIG. 4 illustrates a top-down view of a non-limiting example, showing four different potential locations $P_1$-$P_4$ of the solid state sensor oriented with its sensitive axis tangential to the geometry of the drive coil. Note that the embodiment is not limited in this respect and the probe may comprise any desired number of sensors (i.e. 1, 2, 4 or more sensors may be placed along diameters of the coil with their sensitive axis aligned in the tangential direction). Assuming that the in-plane (i.e., in the page of FIG. 4) length of the sensor represents the insensitive in-plane axis of the sensor and that the arrow over each sensor in FIG. 4 identifies the sensitive axis of the sensor, it is seen that for each of positions $P_1$-$P_4$ the in-plane insensitive direction is coincident with a diameter of the drive coil (represented by the dashed lines) and that the sensitive axis is tangential to the drive coil. Although the in-plane magnetic field due to the incident field and the induced field in a uniform material may be significant at these locations, its orientation is purely radial, and the tangential field is zero unless cracks or other irregularities in the surface disrupt the eddy currents and give rise to a perturbed induced magnetic field.

It should be appreciated that in the configuration of FIG. 4 the sensor 302 (in any of the four illustrated possible locations $P_1$-$P_4$) is de-centered, i.e., not centered within the drive coil. By positioning the sensor more closely to the drive coil perimeter (i.e., by not centering the sensor), the sensitivity of the sensor to small cracks or irregularities may be increased. It should be appreciated that analogous positions also exist outside the coil, illustrated as positions $P_5$-$P_8$. It should also be appreciated that similar positions (i.e. positions where the local direct and induced field is zero along one direction, and non-zero in the presence of a crack or flaw, and in which a sensor may be placed with its sensitive axis aligned with this direction) may be identified for drive coils that are square, rectangular, or of other convenient shapes. It should furthermore be appreciated that this concept may also be utilized with a linear drive wire as opposed to a drive coil, for example to allow for close spacing of the solid state sensor to the drive source (drive coil or linear drive wire).

The detection loop 304 may take any suitable configuration. According to the non-limiting embodiment illustrated, the detection loop 304 may be formed by lead lines connected to the solid state sensor 302 (which may be referred to as "pickup leads") to read out a signal from the solid state sensor. However, not all embodiments are limited to this configuration, as other embodiments allow for the detection loop 304 to be electrically disconnected from the solid state sensor 302. Similarly, the detection loop 304 may be a coil in some embodiments, including any suitable number of turns, and may be formed of any suitable material (e.g., a conducting material such as a metal (e.g., copper as a non-limiting example), a conducting polymer, or other conducting material). Using a larger number of turns for the detection loop may increase the signal generated by the detection loop. As shown, the detection loop 304 may be arranged around (e.g., wrapped around), or at least partially around, the substrate 306 on which the solid state sensor is disposed. As will be described further below, the detection loop may be small in some embodiments, and thus may be a microscopic loop in some embodiments. For example, the detection loop may have a small height h (e.g., the dimension substantially parallel to the axis of the drive coil) and/or the detection loop may enclose a small area. In embodiments in which the detection loop is arranged around the substrate, the height of the detection loop may be determined by the thickness of the substrate and, thus, the area enclosed by the detection loop is also determined, in part, by the thickness of the substrate.

In one embodiment, the detection loop 304 may be formed by interconnecting metal traces on different layers of a printed circuit board using vias or in any other suitable manner, as described further below. In such an embodiment, the drive coil may also be formed on the PCB, though not all embodiments in which the detection loop is formed on a PCB are limited in this respect. In those embodiments in which the detection loop and/or drive coil are formed on a PCB, the substrate 306 may be omitted (or, alternatively, the PCB may be considered to be the substrate 306).

As with the solid state sensor 302, the detection loop 304 may be designed to be insensitive to the magnetic field created by the drive coil, thus increasing the ability of the detection loop to detect perturbations in the induced magnetic fields associated with eddy currents in a material under test. For example, as can be seen from the embodiment of FIG. 3, the principal axis of detection loop 304 may be substantially perpendicular to the principal axis of the drive coil (e.g., the principal axis of the detection loop may be in the x-direction while the principal axis of the drive coil is in the z-direction). Other configurations are possible, however, as a substantially perpendicular orientation of the detection loop relative to the drive coil is one non-limiting example (e.g., the two may have principal axes oriented at 20 degrees relative to each other, 30 degrees relative to each other, 45 degrees relative to each, 60 degrees relative to the each other, 75 degrees relative to each other, or any other suitable angle (e.g., any suitable angle between approximately 10 degrees and 170 degrees)).

For example, according to one embodiment, the detection loop 304 may be placed along a coil diameter with its principal axis (and therefore its sensitive direction) oriented along a substantially tangential direction, analogous to the positioning of hybrid sensors in FIG. 4 as discussed above.

Figure 2:
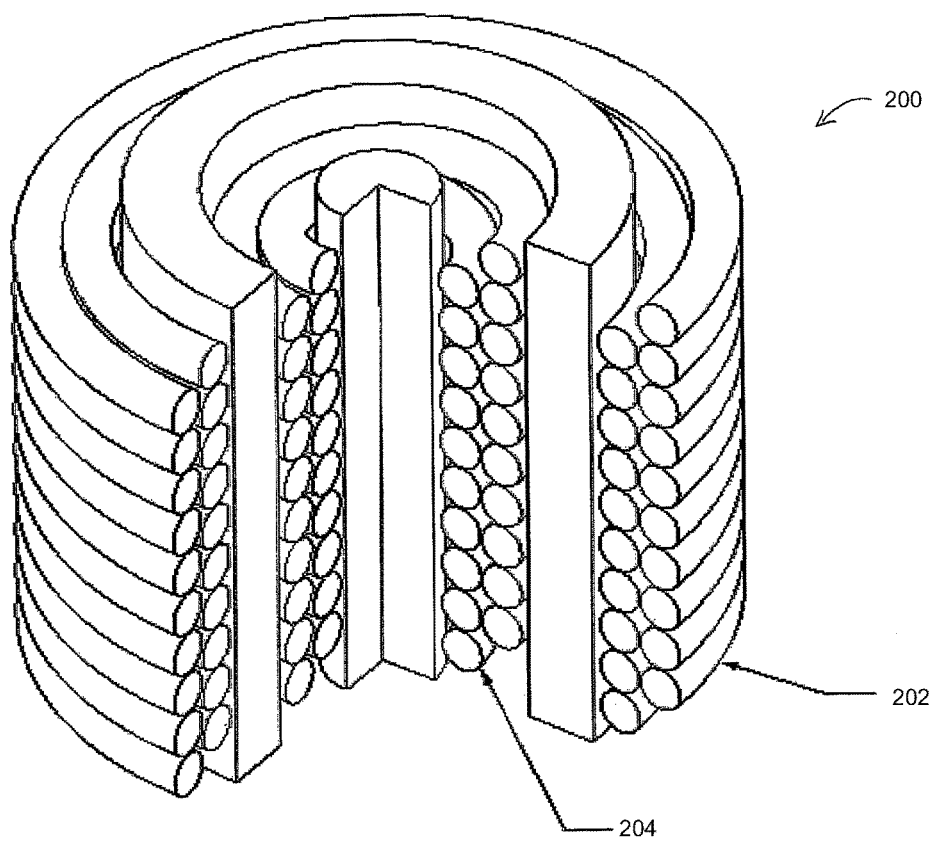
FIG. 2 illustrates a second type of conventional coil-based eddy current probe having distinct, co-axial drive and detection coils.

The drive coil may be any suitable drive coil, such as those conventionally used in eddy current probes of the types shown in FIGS. 1 and 2. The drive coil may be a pancake coil in some embodiments. The drive coil may have any suitable shape, including circular (e.g., as shown in FIG. 4), square, and rectangular, among others.

In the non-limiting example of FIG. 3, the drive coil may be larger than the substrate 306 and thus may be stabilized on its own support structure. However, not all embodiments are limited in this respect. For example, according to some embodiments, the drive coil may be disposed on or in the same substrate 306 as that on or in which the solid state sensor 302 is disposed. For example, the drive coil may be formed on a top surface of the substrate and/or on the bottom surface of the substrate (e.g., See FIG. 6).

One or more of the following benefits, among others, may be realized by the configuration of an eddy current probe of the type illustrated in FIG. 3. First, the orientation of the drive coil to be substantially parallel to the surface of the material under test when in use may maximize the coupling between the drive coil and the material under test, thus creating large eddy currents. Secondly, the orientation of the detection loop to be substantially perpendicular to the surface of the material under test when in use may maximize the sensitivity of the detection loop to the magnetic field components parallel to the surface caused by cracks or other flaws. Thirdly, the relative orientation of the detection loop perpendicular to the drive coil may minimize the direct coupling between the drive coil and the detection loop. Fourth, the orientation of the detection loop to detect the magnetic flux associated with eddy currents in the material under test may complement detection of the defect by the solid state sensor, especially at high frequencies. In that manner, a single probe may be utilized to cover a wide range of frequencies, with the signal from the solid state sensor (AMR, GMR, or other) dominating at frequencies below a transition frequency and the signal from the detection loop dominating above the transition frequency. The transition frequency may be design dependent and may occur around 1 MHz. Thus, probes of the types described herein may operate with large frequency bandwidths.

Eddy current detection probes of the type illustrated in FIG. 3 can be of any suitable size. In some embodiments, the eddy current detection probes may be small. A non-limiting example of dimensions of some of the components is now given. As shown in FIG. 3, in one non-limiting embodiment, the substrate 306 may be less than or approximately equal to 1000 microns wide. The substrate 306 may have a thickness of less than or approximately equal to 500 microns. The solid state sensor may have a strip 310 that is less than or approximately equal to 250 microns long (e.g., in the x-direction of FIG. 3), a width (e.g., in the y-direction of the side view of FIG. 3) that is less than or approximately equal to 8 microns, and a thickness (e.g., in the y-direction of the side view of FIG. 3) that is less than or approximately equal to 30 nanometers. Such dimensioning of the solid state sensor may result in the solid state sensor being sensitive to magnetic fields only along one axis (e.g., only along the y-direction in the side view of FIG. 3). Other dimensions for the solid state sensor are also possible, as the numbers listed above represent non-limiting examples.

The detection loop may have any suitable size, and in some embodiments may be a microscopic loop. According to one embodiment, the detection loop 304 may enclose an area of less than or approximately equal to 1000 microns by less than or approximately equal to 500 microns, an area of less than or approximately equal to 0.50 mm$^2$; according to another embodiment, the detection loop 304 may enclose an area of less than or approximately equal to 0.20 mm$^2$. According to some embodiments, the detection loop 304 has a small height (e.g., dimension h in FIG. 3). For example, the height of the detection loop may be less than or approximately equal to 250 microns; and, in some embodiments, less than or approximately equal to 150 microns.

According to one embodiment, probes of the type illustrated in FIG. 3 and utilizing a detection loop in combination with a solid state sensor may be formed on a printed circuit board (PCB), flexible printed circuit board or other three dimensional membrane.

In operation, the eddy current detection probe 300 may be placed in proximity to a material under test to test for the presence of cracks or other defects. The drive coil may be excited with an AC current, thus generating an incident magnetic field which impinges upon the material under test. The excitation frequency may have a broad range and in some instances may exceed 1 MHz although not all embodiments are limited in this respect. Eddy currents may thus be generated in the material under test, and the eddy currents may generate induced magnetic fields; cracks or other irregularities in the surface may generate magnetic field components parallel to the surface of the material under test which are detected by the combination of the solid state sensor and the detection loop.

In those embodiments in which the solid state sensor is an AMR sensor, the resistance of the AMR sensor may vary in dependence on the magnetic field where the sensor is located. Such variations in the resistance value may be detected by changes in a signal read from lead lines of the AMR sensor (e.g., from the detection loop in those embodiments in which the detection loop comprises the lead lines). In addition, the detection loop may enclose some of the magnetic flux associated with the induced magnetic fields. Changes in the magnetic flux due to the eddy currents induce a voltage in the detection loop which may be detected by suitable readout electronics (not shown). Thus, in the example of FIG. 3, both the solid state sensor and the detection loop contribute to the total detection signal output by the lead lines forming the detection loop and therefore both contribute to detection of magnetic fields associated with eddy currents in the material under test.

However, as previously mentioned, it should be appreciated that not all embodiments are limited to the detection loop being electrically connected to the solid state sensor as lead lines of the solid state sensor. Rather, in some embodiments the detection loop may be electrically distinct from the solid state sensor (e.g., the solid state sensor may have its own dedicated lead lines). In such an embodiment, distinct signals may be output by the solid state sensor and the detection loop and may be processed in any suitable manner (e.g., processed individually, combined and processed, etc.) to assess whether the induced magnetic fields indicate the presence of a crack or other defect in a material under test.

The relative magnitude of a signal output by the solid state sensor 302 compared to a signal output by the detection loop 304, or the relative magnitude of contributions to a single signal attributable to the solid state sensor and the detection loop (i.e., in those embodiments in which a single signal is provided by the solid state sensor and detection loop), may depend on various factors. To first order, a solid state (AMR, GMR, or other) sensor is sensitive to the field H, and the detection loop to the product of frequency f, field H, the number of turns in the detection loop, and the area enclosed by the loop A. Thus, in those embodiments in which the solid state sensor 302 is an AMR sensor or GMR sensor, the contribution of the detection loop may become significant and in fact dominant over that of the solid state sensor at drive coil frequencies above a transition frequency which depends on the specific design of the sensor and the detection loop. For example, the contribution from the detection loop may become substantial above 500 kHz or at frequencies greater than approximately 1 MHz.

Figure 5:
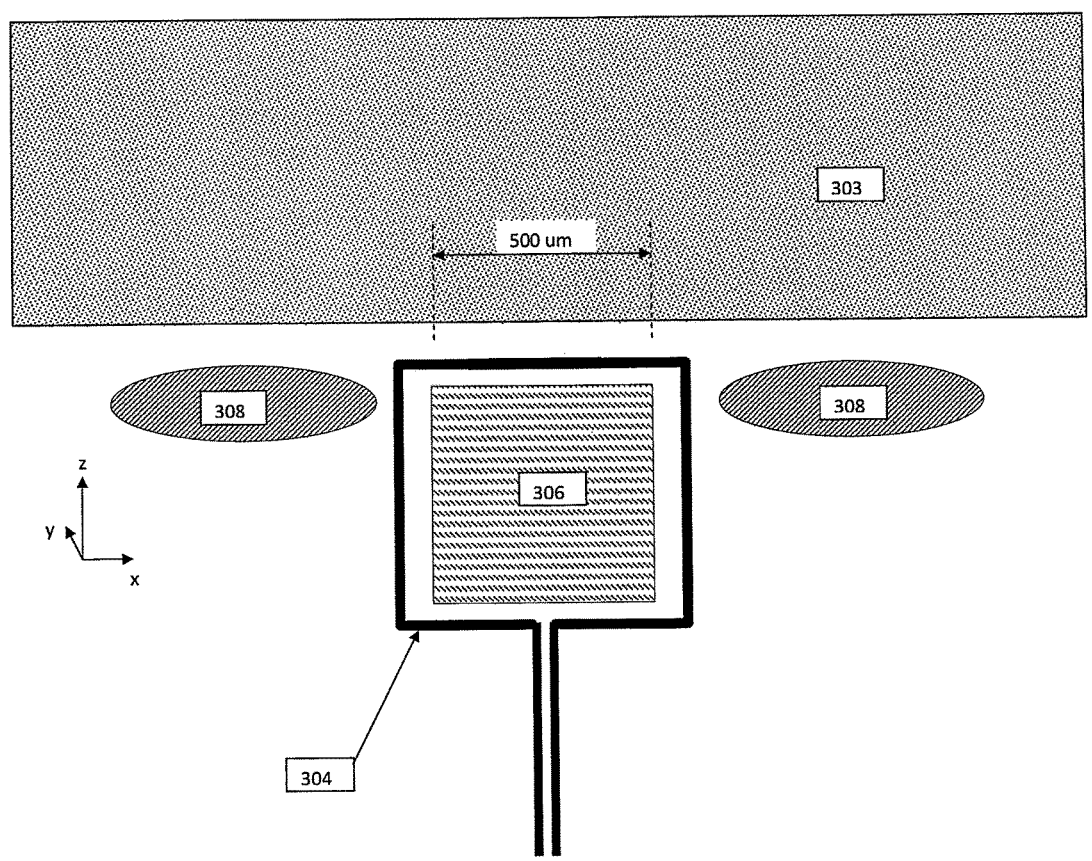
FIG. 5 illustrates an eddy current detection probe including a drive coil and a detection loop according to another non-limiting embodiment.

The inventors have realized that some applications do not require the use of a solid state sensor. A non-limiting example is illustrated in FIG. 5. As shown, the eddy current detection probe 500 includes the detection loop 304, substrate 306, and drive coil 308 of FIG. 3. However, the eddy current detection probe 500 differs from the eddy current detection probe 300 of FIG. 3 in that no solid state sensor is included. Such a probe design may be suitable in situations in which the output signal of the detection loop is sufficient to exceed any anticipated noise level, such that the solid state sensor 302 of FIG. 3 is not needed to overcome the noise level. Additionally, the substrate 306 may optionally be omitted as it may not be needed to support the detection loop 304 (e.g., the detection loop 304 may be formed without enclosing any substrate).

According to one aspect, an eddy current detection probe includes a drive coil and a detection loop, with the detection loop having a principal sensitive axis (also referred to herein as the "axis of sensitivity") that is not aligned with the principal axis of the drive coil. As in the case of the hybrid sensor discussed above, the detection loop and drive coil may be oriented relative to each other in any suitable manner to: (a) minimize detection of the incident magnetic field by the detection loop; and/or (b) increase the sensitivity of the detection loop to perturbations in the induced magnetic fields associated with cracks or other defects in a material under test.

The detection loop may have a principal sensitive axis oriented to be non-parallel with the principal axis of the drive coil 308. For example, in the non-limiting embodiment of FIG. 5, the drive coil 308 may have a principal axis oriented in the z-direction. The detection loop may have a principal axis oriented in any direction other than the z-direction. By configuring the drive coil and detection loop such that their principal axes are not parallel to each other, the sensitivity of the detection loop to magnetic fields generated by the drive coil may be minimized and the sensitivity of the detection loop to perturbations in the induced magnetic fields due to defects such as cracks in a material under test may be increased.

According to one non-limiting embodiment, the detection loop 304 is substantially perpendicular to the drive coil 308, in that the principal axis of the detection loop is perpendicular to the principal axis of the drive coil. In some embodiments, the principal axis of the detection loop may be oriented at an angle of between 10 degrees and 170 degrees (e.g., 30 degrees, 45 degrees, 60 degrees, 75 degrees, 90 degrees, 105 degrees, 120 degrees, between approximately 30 degrees and 90 degrees, between approximately 60 degrees and 90 degrees, or any other suitable angle) relative to a principal axis of the drive coil.

Referring to FIG. 5, a substantially perpendicular relative orientation of the drive coil and detection loop is shown, as the principal axis of the detection loop may be in the y-direction and the principal axis of the drive coil may be in the z-direction. Such a perpendicular configuration may be beneficial, for example by maximizing the sensitivity of the detection loop to perturbations in the magnetic fields generated by cracks or other defects in a material under test parallel to the drive coil and by minimizing the sensitivity of the detection loop to the magnetic fields generated by the drive coil.

Figure 6:
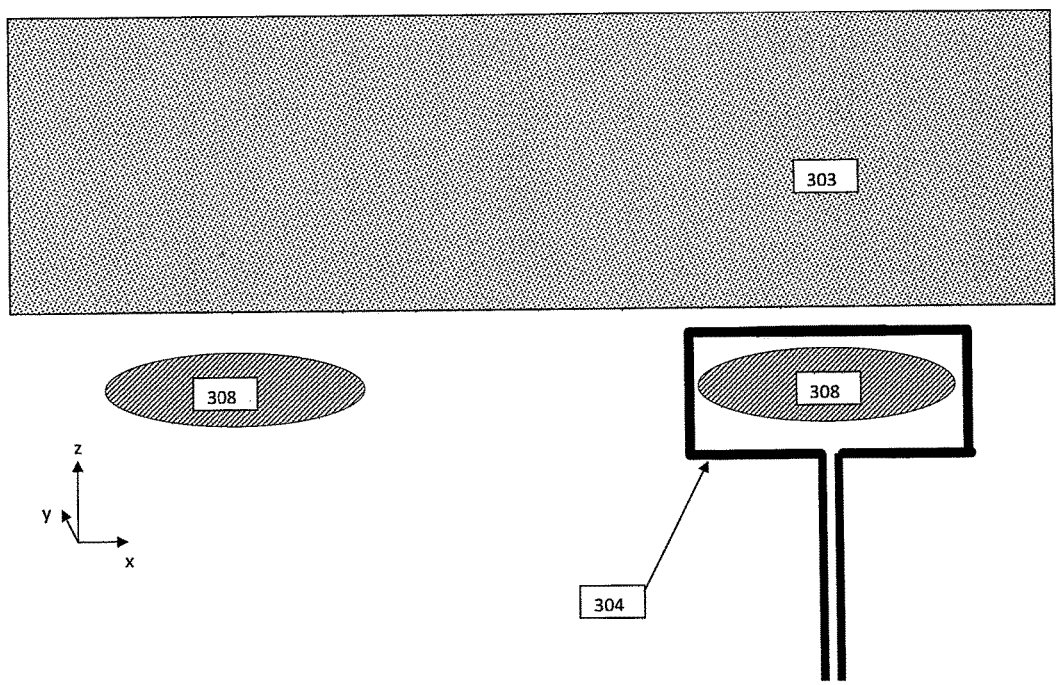
FIG. 6 illustrates an eddy current detection probe including a drive coil and a detection loop which surrounds the conductor of the drive coil.

According to one embodiment, the detection loop may surround the drive coil or wire. FIG. 6 illustrates one non-limiting case. The figure shows a cross section taken in the plane of the detection loop 304. The drive wire 308 passes through the center of the area enclosed by the detection loop. This geometry is a limiting case of the geometry illustrated in FIG. 4.

Figure 7:
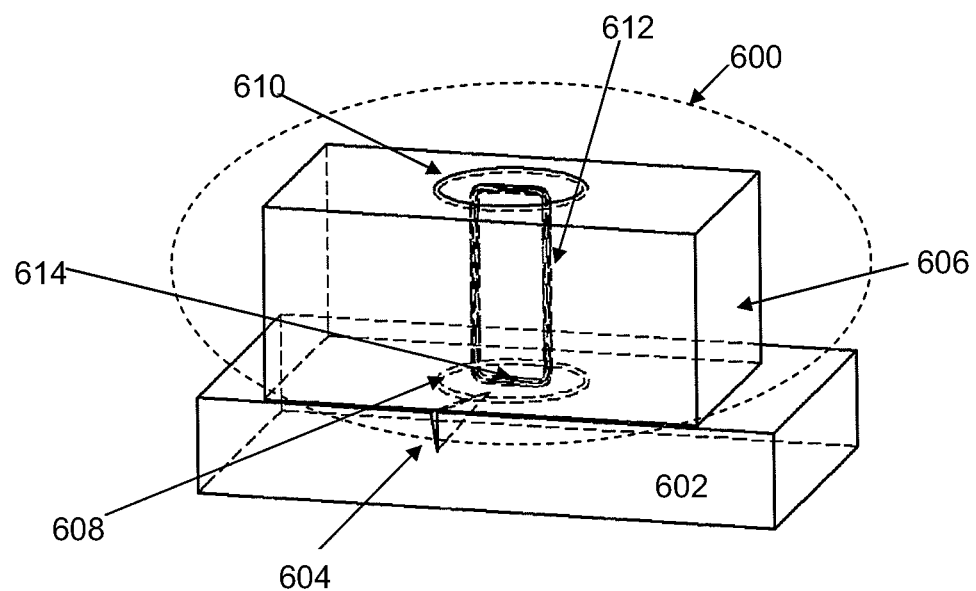
FIG. 7 illustrates an eddy current detection probe including a drive coil and a detection loop according to another non-limiting embodiment.

FIG. 7 illustrates a variation on the eddy current detection probe of FIG. 5. As shown, the eddy current detection probe 600 is placed in proximity to a material under test 602 including a defect 604. The probe 600 includes a membrane 606 (which may also be thought of as a substrate) formed by a sandwich structure of conductive layers and resistive layers. A drive coil 608 is placed on a top surface of the membrane 606 and a drive coil 610 is placed on a bottom surface of the membrane 606. A detection loop 612 is oriented substantially vertically within the membrane 606 and thus is substantially perpendicular to the drive coils 608 and 610.

As can be seen in FIG. 6, according to one embodiment a side 614 of the detection loop 612 may be in substantially the same plane as the drive coil. For instance, as shown, the membrane 606 may have a substantially planar top surface on which the drive coil 608 is disposed. The side 614 of the detection loop 612 may be disposed on the top surface as well, thus making the side 614 co-planar with the drive coil 608. Other configurations are also possible, however, as the shown configuration is a non-limiting example.

The probe 300 of FIG. 5 may be operated at high frequencies in some situations, which may, for example, increase the detection signal from detection loop 304. As mentioned previously, it may be desirable to probe a material under test using high frequency incident magnetic fields, for example if the material under test is a low conductivity material. Generation of a high frequency incident magnetic field may be accomplished by exciting the drive coil 308 with a high frequency alternating current (AC) signal. The resulting induced magnetic fields in the material under test detected by the detection loop 304 may therefore also be high frequency fields. Detection loop 308 may output larger signals in response to detection of higher frequency fields, such that use of high frequency magnetic fields may facilitate detection of certain types of flaws.

According to one embodiment, an eddy current detection probe of the type illustrated in FIG. 5 may be excited with AC drive signals between approximately 500 kHz and 10 MHz, or of any other suitable value. However, it should be understood that lower frequencies (e.g., frequencies between 100 Hz and 500 KHz) may also be used in certain embodiments. One feature of the eddy current detection probes described herein is that they are capable of being excited with AC drive signals over a broad range of frequencies. For example, the probe may be excited with AC drive signals between 100 Hz and 10 MHz; in some embodiments, between 1 KHz and 10 MHz, and in some embodiments, between 10 KHz and 10 MHz. The frequency used to excite the probe may depend on the application in which it is used. Operation over such a broad frequency range enables the eddy current detection probes to be used in a wide variety of applications. Furthermore, the method is not limited to using such frequencies for any particular purposes (e.g., detecting cracks in low conductivity materials being one non-limiting example). Furthermore, it should be appreciated that such methodology may also be applied to eddy current probes of the type illustrated in FIG. 3 including a solid state sensor in addition to a detection loop.

Figure 8:
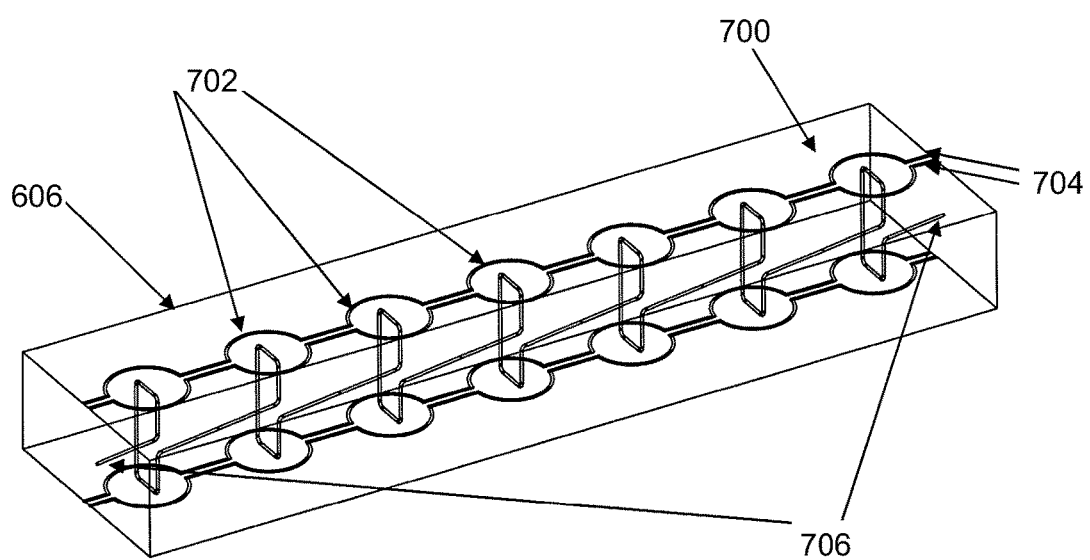
FIG. 8 illustrates an eddy current detection probe including an array of drive coils and detection loops according to another non-limiting embodiment.

According to another aspect, an array of probes of the types previously described herein may be formed. FIG. 8 illustrates a non-limiting example.

As shown, the array 700 may include multiple drive coil-detection loop combinations 702. In the embodiment shown, eight such combinations of the type of probe illustrated in FIG. 7 are included (i.e., eight combinations of drive coils and detection loops). In this manner, a larger area of the material under test may be investigated at a single time. It should be understood that other combinations are also possible. While the array 700 illustrates drive coils and detection loops of the type illustrated in FIG. 7, it should be appreciated that the aspects described herein relating to arrays of eddy current detection probes are not limited in this manner. For example, an array of the type illustrated in FIG. 8 may be formed using multiple probes of the type illustrated in FIG. 3 (i.e., multiple probes each including a solid state sensor and detection loop). Other configurations are also possible.

The drive coils and detection loops of the array 700 may be electrically connected or separate. Namely, the drive coils may be driven together or separately. If driven together (and therefore not sequentially) the drive coils may be electrically connected via a single set of lead lines (e.g., lead lines 704). If driven separately, separate lead lines may be connected to each of the drive coils. If driven separately, the drive coils may be driven simultaneously or at different times (e.g., sequentially, in groups of two or more at a time, or otherwise time divided). Similarly, the detection loops may be read out together or separately. In one example the detection loops may be read substantially simultaneously in contrast to conventional systems in which, due to the mutual inductance of the sensors, sequential excitation of drive coils and sequential reading of sensors is needed. In the situation in which the detection loops are read out together, they may be electrically connected and read by a single set of lead lines (e.g., lead lines 706). If the detection loops are read out separately, each loop may be connected to its own set of lead lines, and the loops may be read out at any suitable relative timing (e.g., simultaneously, sequentially, in groups of two or more at a time, or otherwise time divided, etc.). Thus, it should be appreciated that the array of drive coils and detection loops may be operated in any suitable manner.

Figure 9:
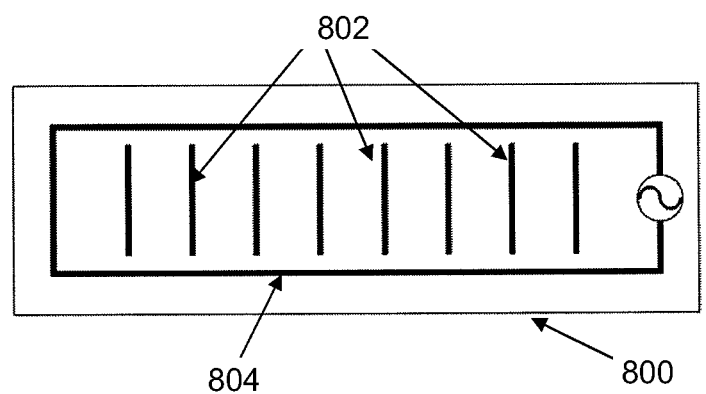
FIG. 9 illustrates an eddy current detection probe including an array of solid state sensors with a single drive coil, according to another non-limiting embodiment.

Moreover, according to one embodiment, an array of solid state sensors and/or detection loops may be used with a single drive coil. An example is illustrated in FIG. 9. As shown, an eddy current detection probe 800 may include multiple (i.e., eight in this non-limiting case) solid state sensors 802 of the type in FIG. 3 in combination with a single drive coil 804. In this example, the drive coil 804 is rectangular in shape, though other shapes may alternatively be used. According to one embodiment in which a single drive "coil" is used with an array of sensors, the drive "coil" may be a linear drive wire. Since all the sensors operate in connection with a single drive coil/wire, sequential scanning of the sensor outputs may be avoided.

Using one or more of the aspects described above with respect to arrays of sensors, improved speed in scanning a material under test may be provided compared to conventional sensors. For example, the sensors of the array may be configured in a linear or multidimensional array so that an image of the eddy currents and defects in a material under test can be created without moving or scanning the sensors relative to the material under test.

According to another aspect, a linear drive wire, as opposed to a drive coil, for generating an incident magnetic field and therefore the eddy currents in a material under test is provided. For example, referring again to the non-limiting embodiment of FIG. 9, the drive coil may be formed as a drive wire, for example by including only one of the sides of the coil illustrated. For example, the side of the coil 804 under the array of solid state sensor 802 in the figure may be retained.

In utilizing eddy current detection probes having solid state sensors of the types previously illustrated, it may be beneficial for the solid state sensor to be as close to the drive coil as possible, since such positioning may result in a stronger detection signal from the solid state sensor. However, with such solid state sensors, it is also preferable in some situations, as previously described, for the solid state sensor to be approximately centered within the drive coil. Thus, in situations in which a drive coil has a substantially closed geometry (e.g., a circular geometry, a rectangular geometry, etc.), a design in which the solid state sensor is to be centered within the drive coil places a limitation on how close the solid state sensor can be to the drive coil, since moving the solid state sensor closer to one portion of the drive coil may result in de-centering of the solid state sensor. Thus, competing design constraints may come into play.

In view of such competing design constraints, one aspect provides a linear drive wire rather than a drive coil. In this manner, a sensor (e.g., a solid state sensor alone, a solid state sensor in combination with a detection loop having a cross section perpendicular to the drive wire, or a detection loop alone) may be positioned more closely to the drive wire than would be possible using a drive coil, and therefore the sensor may be able to produce stronger detection signals than would be otherwise possible, thus allowing for detection of smaller defects. In such a configuration in which a linear drive wire is used, there is no need to center the sensor with respect to the drive wire (i.e., the sensor can be to the right or left of the drive wire or the detection loop may enclose the drive wire and the sensor will operate appropriately).

The eddy current detection probes described herein may be formed/manufactured in any suitable manner. According to one aspect, drive coils and/or or detection loops of the types described herein may be formed on multilayered substrates by interconnecting traces on various layers of the substrate. For example, substrate 306 shown in FIGS. 3 and 5 may be a multi-layered substrate, for instance being a multi-layered printed circuit board (PCB). Conductive traces on various ones of the layers may be interconnected using conductive interconnects to form the drive coil (e.g., in those embodiments in which the drive coil is formed on substrate 306) and/or the detection loop. For example, the traces on the surface of a substrate may form the geometry of the detection loop and/or drive coil in a plane. Multiple layers of this substrate can form multiple planes, on which many drive coils and/or detection loop turns and connecting traces can be constructed. Conductive holes (i.e. "vias") in each layer, or through all layers, can form the interconnections between detection loop/drive coils, create multiple turns in the substrate plane, or form the closed path for loops/coils perpendicular to the substrate plane. In some embodiments, this may allow for arbitrary structures in the substrate plane (i.e. circles), but may restrict the detection loop/drive coil structures to rectangles in the perpendicular plane, because of the limitation that holes are typically straight. If the detection loop geometry is much finer than the driver coil, the conductive layers for the detection loop can be formed by a different process with thinner conductive material and finer trace width, spacing, and via size. In at least some embodiments, the detection loop does not require high current carrying capacity.

According to some embodiments, substrates can be made of almost any non-conductive material that can be drilled and layered with etchable conductive material. Some non-limiting examples include FR4 epoxy, polyimide, silicon, ceramic, and Teflon. Highly conductive materials such as copper, silver, gold, conductive polymer or graphene may form the detection loops and/or drive coils in at least some embodiments.

Thus, it should be appreciated that eddy current probes of the types described may be formed using printed circuit board and/or photolithographic techniques (e.g., traces and/or coils may be defined photolithographically according to standard microfabrication processing techniques).

Similarly, a hybrid eddy current detection probe including a solid state sensor (e.g., an AMR sensor) and a detection loop may be made by placing the AMR inside a conductive driver coil with fine placement precision. Hand wound coils present the problem of having to mechanically align the AMR sensor such that crosstalk is minimized. If a photolithographically fabricated drive coil is used, it, the detection loop, and connecting traces that are part of the hybrid eddy current detection probe may be etched with standard printed circuit board and/or microfabrication process steps as part of the sensor fabrication. As an alternative, connection pads and alignment points can be fabricated together as part of one multi-step process to facilitate accurate placement of a separately diced silicon AMR sensor. In this way, a flexible backing may be used and complex, custom sensor arrays may be made with standard AMR cells.

Use of the fabrication techniques described above may allow for various possible constructions scenarios, some of which have been previously described. For example, the detection loop(s) may be fabricated within the drive coil(s) or around the drive coil(s). Detection loops may be wrapped around a conductor serving as a drive coil (e.g., when the drive coil is a straight trace, i.e., a drive wire.) The drive coils and detection loops may take various suitable shapes, including rectangular, diamond-shaped, wave-shaped, and parabolic curve shaped, among others. The drive coils may include any suitable number of turns. Multiple differential matching detection loops may be fabricated.

As non-limiting examples, a four turn driver coil can be constructed with one circular turn on the $1^{st}$ (top), $3^{rd}$, $4^{th}$ and $6^{th}$ layers of a 6-layer process. One or two substrate layers may separate each coil turn and conductive holes (vias) may connect the turns in such a way as to create a stepped helix. Such a geometry may be beneficial for thicker, current carrying driver coils. Detection loops may be constructed perpendicular to the layers using the $2^{nd}$ and $5^{th}$ conductive layers with vias completing the rectangular loops. Connecting traces can come inside the driver coil on these layers to connect the many turn loop to sensing electronics.

It should be appreciated that the relative sizes of the drive coils and detection loops are not limiting. In some embodiments, such as shown in FIGS. 3 and 5, the detection loop may be positioned "inside" the drive coil, in that the detection loop may be within the diameter of the drive coil. Alternatively, the detection loop may have at least one dimension larger than the drive coil, and the drive coil may be "inside" the detection loop. Such configurations represent two non-limiting possibilities.

According to another aspect, any of the eddy current detection probes previously described may be flexible. For example, drive coils/wires, solid state sensors (e.g., AMR sensors), and/or detection loops may be formed on flexible materials such as those used for flexible circuit boards or other conductive membranes. As a non-limiting example, the substrate 306 in FIG. 3 may be flexible and the solid state sensor 302 and drive coil 308 may be disposed on the flexible substrate. In some embodiments, the flexible substrate may be curved during use, as described further below. In another non-limiting example, the substrate 306 may be rigid or substantially rigid, but may be disposed on a larger flexible substrate, allowing for wrapping of the flexible substrate around a material under test (e.g., multiple rigid substrates 306 may be positioned in an array on a larger flexible substrate). Other configurations of flexible eddy current detection probes are also possible.

The eddy current detection probes may be used to identify defects in a wide variety of articles. In some embodiments, the probes are particularly useful in identifying smaller defects (e.g., defects having a size of less than or approximately equal to 500 micron, less than or approximately equal to 250 micron, or less than or approximately equal to 100 micron). The probes may also be used to identify defects that are located close to, or at, the surface of the article being tested. In general, the articles tested by the probe may be formed of any material having a suitable conductivity (e.g., a metal, metal alloy) which enables generation of eddy currents within the material. Advantageously, the probes described herein are able to identify defects in relatively low conductivity metals and metal alloys including titanium and Inconel®, amongst others. A wide variety of different types of articles may be tested using the probe. Particularly well-suited articles include those used in heat exchanger applications and jet engine applications. The use of flexible eddy current detection probes may allow for inspection of articles having curved surfaces. For example, flexible eddy current detection probes may be positioned against a curved surface (e.g., tubes including heat exchanger tubes, inside a bore hole, against an airplane wing, etc.) allowing for analysis of typically difficult to reach parts of materials under test.

According to another aspect, a bucking circuit is provided for operation in connection with eddy current detection probes of the types previously described (e.g., eddy current detection probes of the types shown in FIGS. 3, 5, and 7). The drive signals typically used to drive the drive coil of an eddy current detection probe are sinusoidal in nature. Thus, the detected signal (or "detection signal) from a solid state sensor or detection loop of the types described herein may also be sinusoidal in nature. Moreover, there may be other sinusoidal signals of the same frequency present in the system due, for example, to inductive pickup in the leads, eddy currents in unperturbed material, or residual coupling between the sensor and/or detection loop and the drive coil. It should be appreciated that such signals may be apparent in the output of the detector in the absence of cracks. The detection signals produced by eddy current detection probes according to the various aspects described herein may change amplitude and/or phase when a defect is encountered in a material under test. Such changes in amplitude and/or phase of the detection signal may allow for detection of a defect.

The inventors have appreciated that the deviations from the quiescent signal when a defect is encountered are typically relatively small. Thus, the inventors have appreciated that the deviations from the quiescent signal may be detected by recording a reference signal in a region where there is no crack or defect and subtracting an inverted sinusoid equal and opposite to the reference signal from the detection signal (also referred to herein as an "output signal"). The inverted sinusoid cancels the substantially constant (i.e. not due to the crack or defect) portion of the output signal, thus leaving a substantially null signal except for deviations from a zero value when a defect is encountered.

According to one aspect, a bucking circuit is provided for performing the signal processing described, namely subtracting an inverted sinusoidal signal from a detection signal.

The detection signal may be pre-conditioned, for example, by applying a bucking signal (e.g., at the drive frequency). The bucking signal may comprise an inverted reference signal. The reference signal may be obtained by making a reference measurement at a point of the article being tested known to be free of defects. The reference signal may be obtained by averaging the respective signals obtained at several different such points of the article being tested. The bucking signal can allow more efficient utilization of the bit depth of the digitizing electronic circuit.

Figure 10:
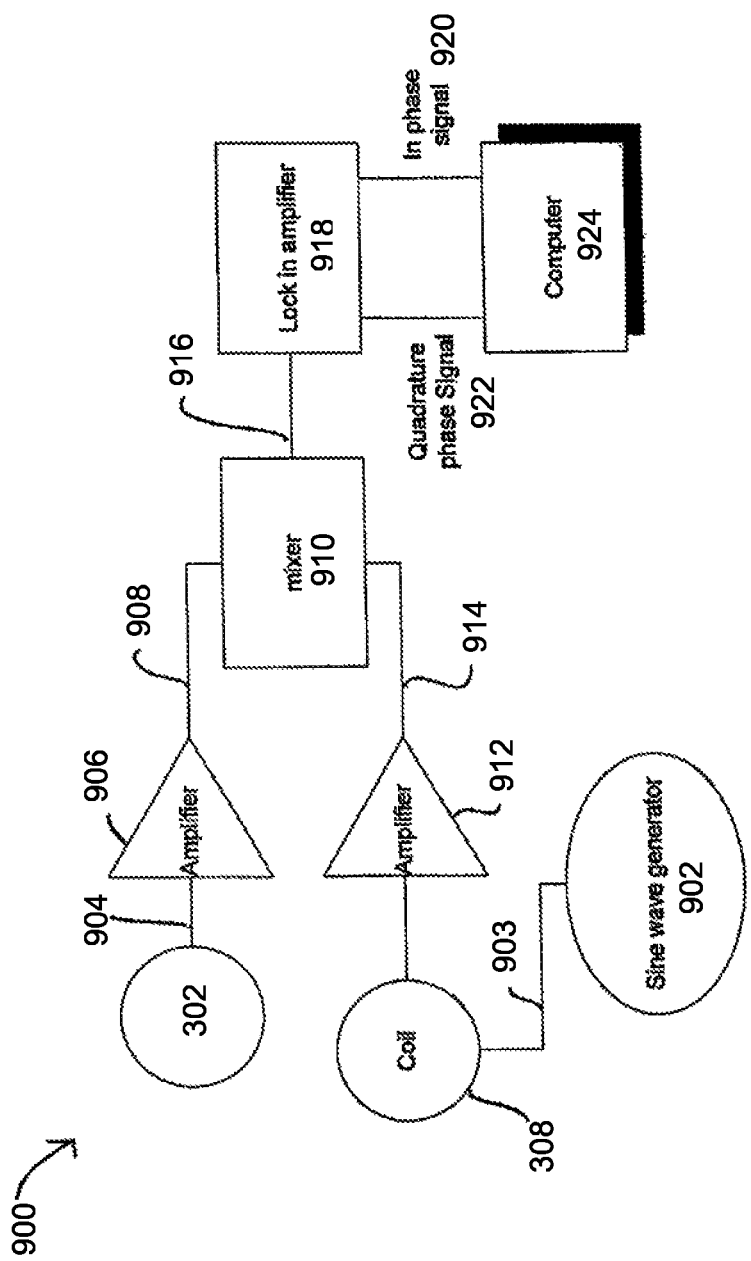
FIG. 10 illustrates a non-limiting example of a block diagram of a bucking circuit that may be used with sensors of the types described herein.

A non-limiting example of a suitable bucking circuit is shown in block diagram form in FIG. 10, which is described in the context of an eddy current detection probe of the type illustrated in FIG. 3, though it should be appreciated that the bucking circuit may be used with the other types of eddy current detection probes described herein as well. As shown, the bucking circuit 900 includes a sine wave generator 902 configured to generate and provide to the drive coil 308 a sinusoidal drive signal 903. The solid state sensor 302 (and in some embodiments, the combination of the solid state sensor 302 and the detection loop 304) generates a detection signal 904. The detection signal is provided to amplifier 906 which may be any suitable amplifier having any suitable gain. The amplifier outputs an amplified detection signal 908 to a combining element 910, e.g. a mixer or a summer. The drive coil signal from sine wave generator 902 is provided to amplifier 912, which may be any suitable amplifier with any suitable gain, and which may in some embodiments be the same type of amplifier as amplifier 906. The amplifier 912 outputs an amplified signal 914 which is provided to the mixer 910.

The mixer 910 combines (by summing or by any other suitable process) the signals 908 and 914 and produces an output signal 916, which is provided to a lock-in amplifier 918. The lock-in amplifier 918 outputs an in-phase signal 920 and a quadrature phase signal 922 to computer 924 which may process the signals in the manner described above to generate a signal that reflects only deviations of the detection signal output by sensor 302 from the sinusoidal shape of the sinusoidal drive signal.

While FIG. 10 illustrates a non-limiting example of a bucking circuit, it should be appreciated that bucking circuits operating in the manner described may take various configurations.

One or more benefits may be realized by using a bucking circuit of the type described in connection with eddy current detection probes of the types described herein. First, better signal-to-noise ratio may be achieved. Secondly, in those embodiments in which an analog-to-digital converter is used to convert the analog output signal of the solid state sensor and/or detection loop into a digital signal, fewer bits may be required since the detection signal has a substantially zero value except for those limited portions of the signal corresponding to when a defect is encountered.

According to another aspect, a detection signal of the eddy current detection probes of the types described herein is analyzed for a particular signature in the image of eddy current produced, related to the geometry of the probe designs described. An example signature is four peaks derived from the in-phase and quadrature signals indicating a particular defect.

Figure 11:
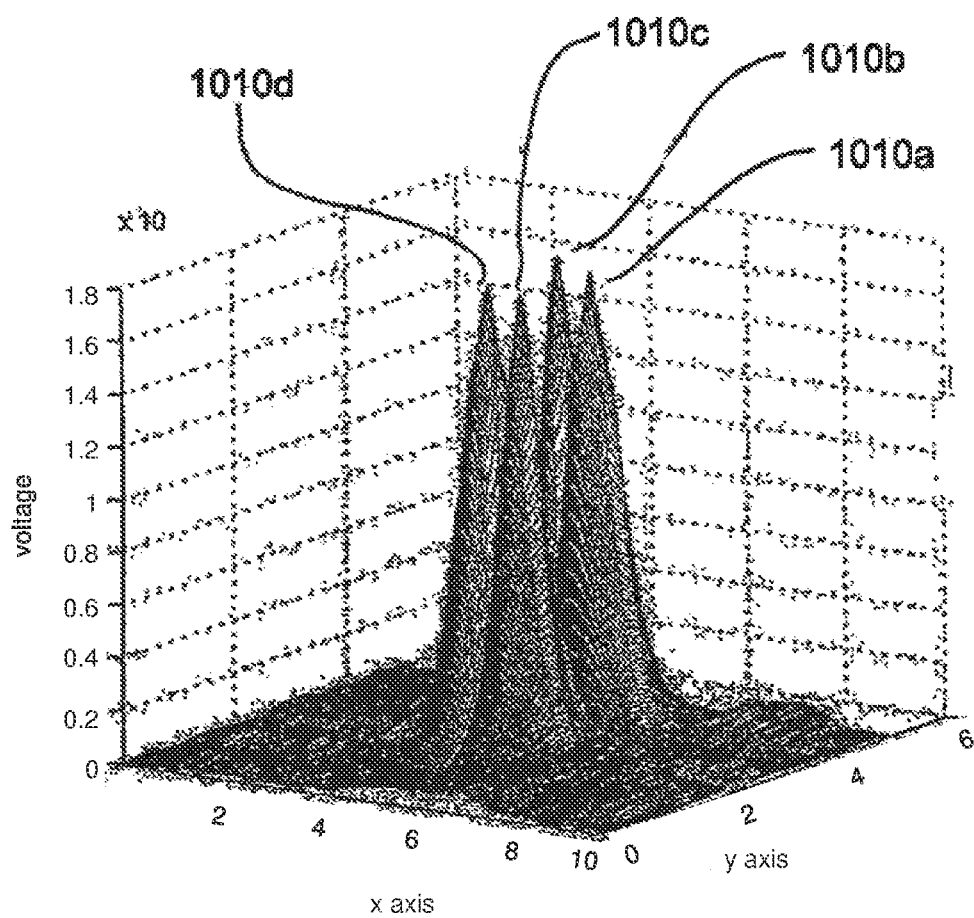
FIG. 11 illustrates an example of a detection signal signature according to embodiments described herein.

Inventors have appreciated that when defects (e.g., cracks) become relatively small in size compared to the size of the drive coil of an eddy current detection probe (e.g., when the length of the crack becomes smaller than the diameter of the drive coil), the detection signal of the probe may include four peaks 1010a-1010d, as shown in FIG. 11, which shows the voltage of the detection signal as a function of space in an x-y plane assuming that the surface of the material under test is disposed in the x-y plane.

Figure 12:
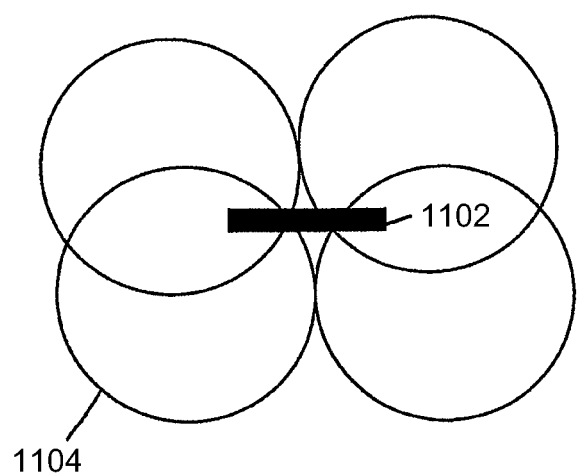
FIG. 12 is an example of the configuration of a crack or other defect relative to the drive coil of an eddy current detection probe as described herein that gives rise to a detection signature including four peaks of the type illustrated in FIG. 10.

FIG. 12 illustrates the cause of the phenomena giving rise to a detection signal pattern of the type illustrated in FIG. 11. In typical operation, the eddy current detection probe, and therefore the drive coil, may be scanned over the material under test in increments (e.g., similar to a raster scan). This may result in the drive coil taking various orientations with respect to a particular defect during the scanning process (e.g., at one point during the scan the right side of a drive coil may be over a particular defect while during a later part of the same scan the left side of a drive coil may be positioned over the defect). In situations in which the defect is smaller than the diameter of the drive coil, a noticeable detection response may be produced only when the drive coil is at each one of four distinct orientations relative to the crack (i.e., at only four different stages of the scanning process). FIG. 12 illustrates an example, in which four distinct locations of a drive coil 1104 relative to a crack 1102 are shown. It should be appreciated that the drive coil assumes only one of the four illustrated positions at any given time during the scanning process. If a noticeable detection response is generated for each of the four illustrated positions of the drive coil, then the resulting detection signal pattern shown in FIG. 11 may be seen.

Thus, according to one aspect, the detection signal generated by an eddy current detection probe may be analyzed for a signature, such as that shown in FIG. 11, which may be indicative of certain types of defects or defects having certain characteristics (e.g., a certain size, etc.).

AMR sensors are field sensitive and directionally sensitive, which makes them suitable for numerous applications in addition to the crack detection application described above. They also have an extremely low noise floor and may be made very small. The directionality of the sensors allows them to be used to detect small field components in the presence of larger fields, for example detecting small changes of the induced fields in the presence of the magnetic field generated directly by the drive coil, as long as the fields of interest have some component orthogonal to the large component of the background field.

It should be understood that for certain applications the optimum geometries may be different from the geometry that is described above for the application of detecting cracks. For example, the inventors have appreciated that AMR based sensors may be used to fabricate a probe suitable for determining the case hardening depth of heat treated parts. For some combinations of material and heat treatment processes, the electrical conductivity of the hardened layer at the surface of the part may be different from the electrical conductivity of the unmodified material at the core. The depth distribution of the eddy currents induced in the part, and therefore also the induced magnetic field, depend on the depth profile of the magnetic permeability and electrical conductivity of the material under test, and therefore the response of a sensor sensitive to the induced magnetic field can be used to determine the thickness of the case hardened layer.

For this application the frequency of operation should be chosen so that the depth distribution of the eddy currents exceeds the thickness of the case hardened layer. In practice this may mean operating at low frequencies (frequencies below 500 kHz, below 100 kHz, or below 50 kHz). At these frequencies the response of the magnetoresistive sensor (e.g. AMR sensor) may exceed that of a conductive detection loop. Furthermore, since the response of the magnetoresistive sensor is not dependent on frequency, the sensitivity of the probe may also be independent of frequency. Because of this property, probes based on AMR sensors are suitable for operation in a mode where the response is sampled at various frequencies, or over a range of frequencies. In situations where the thickness of the hardened layer is unknown it may be advantageous to make measurements at a range of frequencies in order to adequately characterize the conductivity at different depths. Thus AMR based probes are particularly appropriate for this application.

It should be appreciated that for the application of depth profiling, the material to be tested may be uniform, and therefore the eddy current distribution may have the same symmetry as the drive coil. Thus the induced magnetic field will have components in the vertical and radial directions and not necessarily in the tangential direction. The magnetic field generated by the driving current in the drive coil will have components in the same directions, however the relative magnitude of these various magnetic field components will vary depending on the location of the sensor, the direction of sensitivity, and the depth profile of the electrical conductivity and magnetic permeability of the part. This is in contrast to the situation described above for detection of cracks and other flaws, where the in-plane symmetry of the eddy current paths is disturbed and magnetic field components are generated which may not be present in the absence of cracks, for example tangential magnetic field components.

Thus for profiling the depth dependence of the electromagnetic properties of the material, the optimum geometry of the detector relative to the coil can be different from that of the eddy current crack detector described previously. In this case, the sensor would be positioned in a location at which at least one of the magnetic field components has a strong dependence on the depth distribution of the eddy currents. In some cases, this position of maximum sensitivity may be outside the perimeter of the drive coil. In some cases, it may be desirable to place the sensor at a specific height relative to the drive coil, which may be at its center, at its lower surface, displaced toward the part, or at any other height which may be chosen for reasons of sensitivity or convenient fabrication.

The axis of maximum sensitivity of the sensor may be placed in the plane parallel to the surface of the part, in which case it should be aligned in the radial direction, perpendicular to the plane, or at any appropriate angle to the plane in order to maximize the sensitivity of the detector to the depth distribution of the eddy currents. In some cases, it may be expedient to align the sensitive axis in the plane parallel to the surface for reasons of manufacturing and/or reproducibility of results, even if such placement does not maximize the sensitivity of the probe to the eddy current depth distribution.

In some embodiments, the drive coil is configured to be positioned proximate a surface of the article being tested such that an axis of the drive coil is perpendicular to the surface of the article. In some embodiments, the magnetoresistive sensor (e.g. AMR sensor) is constructed and aligned to respond to the electrical conductivity and/or magnetic permeability differences between the material in a layer at the surface of the article and the material in the interior of the article. In some cases, for example, the differences between the electrical conductivity and/or magnetic permeability in a layer at the surface of the article and the material in the interior of the article are due to case hardening of the article; and, in some cases, the differences are due to a coating being applied to the article.

In some embodiments, the drive coil is disposed on a substantially planar surface; and in some embodiments, the sensor may be disposed on the same substantially planar surface as the drive coil. For example, in some cases, the sensor is positioned outside the diameter of the coil.

Figure 13:
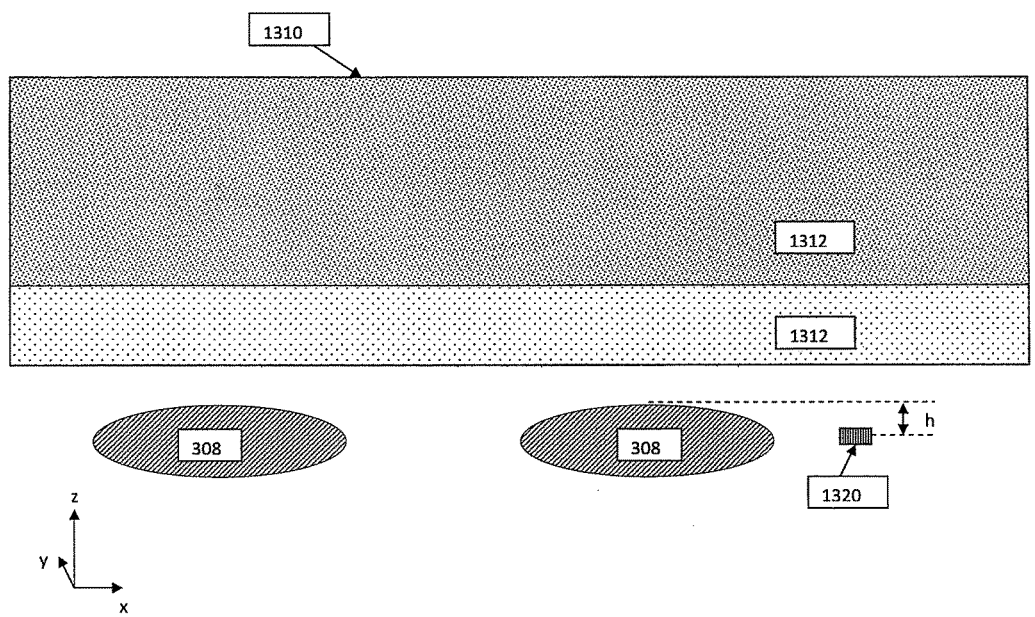
FIG. 13 illustrates an eddy current detection probe for determining the thickness of a surface layer of different electromagnetic properties.

FIG. 13 shows a schematic representation of a probe that may be used for depth profiling. A drive coil 308 in close proximity to the material to be tested has an axis substantially perpendicular to the surface of the part under test. An oscillating electric current is passed through the drive coil, which induces a magnetic field in the part under test 1310. The electromagnetic properties of the part vary with depth, for example due to a case hardened layer 1311 which has different electrical conductivity and/or magnetic permeability than the core material 1312. The distribution of the eddy current density in the part depends on the depth profile of the electromagnetic material properties, for example on the thickness h of the case hardened layer. This eddy current distribution in turn gives rise to an induced magnetic field, which alters the magnetic field in the vicinity of the coil. A magnetoresistive sensor 1320 is positioned in a location and at an orientation chosen to maximize the sensitivity of the probe to the depth of the case hardened layer.

Optionally, multiple sensors may be disposed at different positions relative to the coil to maximize sensitivity, reduce noise, or for redundancy.

The position and orientation of the sensor, the size of the coil, and frequency of operation may be chosen using a mathematical model of the system, which may be analytical or numerical (e.g. using finite element methods). Mathematical models of the system may be used to fit the data obtained as a function of frequency in order to determine the thickness of the case hardened layer from the experimental results. Alternately, the probe may be calibrated against samples with known surface layer thickness.

It should be understood that the configuration used for case hardened layered depth may be useful in determining the depth of other interfaces substantially parallel to the surface of the part, including corroded layers, conductive coatings, or similar surface layers.

Having thus described several aspects, it is to be appreciated various alterations, modifications, and improvements will readily occur to those skilled in the art. Such alterations, modifications, and improvements are intended to be part of this disclosure, and are intended to be within the spirit and scope of the aspects of the invention. Accordingly, the foregoing description and drawings are by way of example only.

What is claimed is:

1. An eddy current detection probe, comprising:
a substrate having a substantially planar surface;
a drive coil disposed on the substantially planar surface;
an anisotropic magnetoresistive (AMR) sensor disposed on the substantially planar surface of the substrate and positioned within a perimeter of the drive coil; and
a detection loop comprising a first electrical lead and a second electrical lead,
wherein the first electrical lead is connected to a first end of the AMR sensor and the second electrical lead is connected to a second end of the AMR sensor,
wherein the first electrical lead and second electrical lead are positioned at least partially around the substrate to form the detection loop, and
wherein a principal direction of sensitivity of the detection loop is oriented substantially perpendicular to a principal axis of the drive coil, wherein the principal direction of sensitivity is a direction of maximum sensitivity.

2. The eddy current detection probe of claim 1, wherein the drive coil is configured to generate the drive magnetic field along a first axis, and wherein the detection loop has a principal sensitivity axis oriented substantially perpendicular to the first axis.

3. The eddy current detection probe of claim 2, wherein a principal direction of sensitivity of the anisotropic magnetoresistive (AMR) sensor is orientated substantially perpendicular to the first axis.

4. The eddy current detection probe of claim 1, wherein the anisotropic magnetoresistive (AMR) sensor and the detection loop are electrically connected to produce a single output signal.

5. The eddy current detection probe of claim 1, wherein the detection loop is configured to apply to, and read from, the anisotropic magnetoresistive (AMR) sensor an electrical signal.

6. The eddy current detection probe of claim 1, wherein the AMR sensor is configured to be sensitive to magnetic fields along only one axis.

7. The eddy current detection probe of claim 6, wherein the AMR sensor is configured to be sensitive to magnetic fields along only one axis through its geometry.

8. The eddy current detection probe of claim 6, wherein the AMR sensor is configured to have a preferred direction of sensitivity or a linear out put by means of barberpole stripes.

9. An eddy current detection probe, comprising:
a first substrate having a substantially planar surface;
a drive coil disposed on the substantially planar surface of the first substrate;
a second substrate smaller than the first substrate, the second substrate having a substantially planar surface;
an anisotropic magnetoresistive (AMR) sensor disposed on the substantially planar surface of the second substrate and attached to the first substrate within a perimeter of the drive coil; and
a detection loop comprising a first electrical lead and a second electrical lead,
wherein the first electrical lead is connected to a first end of the AMR sensor and the second electrical lead is connected to a second end of the AMR sensor,
wherein the first electrical lead and second electrical lead are positioned at least partially around the first substrate to form the detection loop, and
wherein a principal direction of sensitivity of the detection loop is oriented substantially perpendicular to a principal axis of the drive coil, wherein the principal direction of sensitivity is a direction of maximum sensitivity.

* * * * *